United States Patent
Hester et al.

(10) Patent No.: US 11,986,178 B2
(45) Date of Patent: *May 21, 2024

(54) KNOTLESS INSTABILITY ANCHOR

(71) Applicant: Medos International Sarl, Le Locle (CH)

(72) Inventors: Douglas Hester, Raynham, MA (US); Brian Otrando, Cumberland, RI (US)

(73) Assignee: Medos International Sarl, Le Locle (CH)

( * ) Notice: Subject to any disclaimer, the term of this patent is extended or adjusted under 35 U.S.C. 154(b) by 421 days.

This patent is subject to a terminal disclaimer.

(21) Appl. No.: 17/484,608

(22) Filed: Sep. 24, 2021

(65) Prior Publication Data

US 2022/0008063 A1     Jan. 13, 2022

Related U.S. Application Data

(60) Division of application No. 16/151,978, filed on Oct. 4, 2018, now Pat. No. 11,160,545, which is a
(Continued)

(51) Int. Cl.
*A61B 17/04* (2006.01)

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC ........ A61B 17/0401; A61B 2017/0414; A61B 2017/0409; A61B 2017/0412;
(Continued)

(56) References Cited

U.S. PATENT DOCUMENTS 5,904,704 A    5/1999   Goble et al.
5,971,985 A   10/1999   Carchidi et al.
(Continued)

FOREIGN PATENT DOCUMENTS

CN      1378439 A    11/2002
CN    201346220 Y    11/2009
(Continued)

OTHER PUBLICATIONS

[No Author Listed] PushLock® Knotless Anchor for Bankart & SLAP Repair Surgical Technique. Arthrex Brochure, 2008.
(Continued)

*Primary Examiner* — Katherine M Shi
(74) *Attorney, Agent, or Firm* — Mintz, Levin, Cohn, Ferris, Glovsky and Popeo, P.C.

(57) ABSTRACT

Methods and devices are provided for anchoring suture to bone. In one exemplary embodiment, a suture anchor is provided that includes one or more bone-engaging surfaces features and an external sidewall. The external sidewall can allow a suture coupled to the suture anchor and located between the anchor and bone to be movable relative to the suture anchor, even when the suture anchor is partially or fully disposed within a bone hole. Suture threaders and suture anchor drivers are also provided that can be used with the various methods and devices disclosed herein, or with other methods and devices known in the art.

4 Claims, 12 Drawing Sheets

Related U.S. Application Data continuation of application No. 14/996,381, filed on Jan. 15, 2016, now Pat. No. 10,105,133, which is a continuation of application No. 13/331,867, filed on Dec. 20, 2011, now Pat. No. 9,265,494.

(52) U.S. Cl.
CPC .............. *A61B 2017/0414* (2013.01); *A61B 2017/0427* (2013.01); *A61B 2017/0438* (2013.01); *A61B 2017/0445* (2013.01)

(58) Field of Classification Search
CPC ...... A61B 2017/044; A61B 2017/0427; A61B 2017/0458; A61B 2017/0445; A61B 2017/0438; A61B 2017/0459; A61B 2017/0454; A61B 2017/0403; A61F 2/0811; A61F 2002/0852; A61F 2002/0882; A61F 2002/0888; A61F 2/0805; A61F 2002/0829; A61F 2002/087
See application file for complete search history.

(56) References Cited

U.S. PATENT DOCUMENTS

| | | | |
|---|---|---|---|
| 6,508,830 B2 | 1/2003 | Steiner | |
| 6,641,596 B1 | 11/2003 | Lizardi | |
| 8,114,128 B2 | 2/2012 | Cauldwell et al. | |
| 9,265,494 B2 | 2/2016 | Hester et al. | |
| 10,105,133 B2 | 10/2018 | Hester et al. | |
| 2006/0247642 A1 | 11/2006 | Stone et al. | |
| 2006/0253119 A1 | 11/2006 | Berberich et al. | |
| 2008/0147063 A1 | 6/2008 | Cauldwell et al. | |
| 2008/0147064 A1 | 6/2008 | Cauldwell et al. | |
| 2008/0147119 A1 | 6/2008 | Cauldwell et al. | |
| 2008/0255613 A1 | 10/2008 | Kaiser et al. | |
| 2009/0076544 A1 | 3/2009 | DiMatteo et al. | |
| 2009/0076545 A1 | 3/2009 | DiMatteo et al. | |
| 2010/0016892 A1 | 1/2010 | Kaiser et al. | |
| 2010/0185238 A1 | 7/2010 | Cauldwell et al. | |
| 2011/0224727 A1 | 9/2011 | Housman et al. | |
| 2011/0264140 A1* | 10/2011 | Lizardi | A61B 17/0401 606/232 |
| 2013/0158599 A1 | 6/2013 | Hester et al. | |
| 2019/0029667 A1 | 1/2019 | Hester et al. | |

FOREIGN PATENT DOCUMENTS

| | | |
|---|---|---|
| JP | H07-194612 A | 8/1995 |
| WO | WO-03070108 A1 | 8/2003 |
| WO | WO-2007063285 A1 | 6/2007 |

OTHER PUBLICATIONS

[No Author Listed] Swivelock® Anchor System: The Knotless Surgical Technique for Ligament Reconstruction. Arthrex Vet Systems Brochure, 2010.

[No Author Listed] Versalok™ Surgical Technique for Rotator Cuff Repair. DePuy Mitek Brochure, 2007.

Japanese Examination Report in JP Application No. 2012-276542 dated Nov. 15, 2016.

Partial European Search Report issued in EP Application No. 12198241.7, dated Oct. 15, 2015.

Patent Examination Report issued in Australian Application No. 2012261783 dated Nov. 26, 2014.

U.S. Appl. No. 13/331,867, filed Dec. 20, 2011, Douglas Hester et al.

U.S. Appl. No. 14/996,381, filed Jan. 15, 2016, Douglas Hester et al.

U.S. Appl. No. 16/151,978, filed Oct. 4, 2018, Douglas Hester et al.

\* cited by examiner

KNOTLESS INSTABILITY ANCHOR

CROSS REFERENCE TO RELATED APPLICATIONS

The present application is a divisional of U.S. application Ser. No. 16/151,978, filed Oct. 4, 2018, and entitled "Knotless Instability Anchor," which is a continuation of U.S. patent application Ser. No. 14/996,381 (now U.S. Pat. No. 10,105,133), filed Jan. 15, 2016, and entitled "Knotless Instability Anchor," which is a continuation of U.S. patent application Ser. No. 13/331,867 (now U.S. Pat. No. 9,265,494), filed Dec. 20, 2011, and entitled "Knotless Instability Anchor," which are hereby incorporated by reference in their entireties.

FIELD OF THE INVENTION

The present invention relates generally to methods and devices for anchoring soft tissue to bone, and in particular to knotless suture anchors and methods for use.

BACKGROUND OF THE INVENTION

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors, and tacks. In soft tissue re-attachment procedures utilizing screws, the detached soft tissue is typically moved back into its original position over the bone. The screw is then screwed through the soft tissue and into the bone, with the shank and head of the screw holding the soft tissue to the bone. Similarly, in soft tissue re-attachment procedures utilizing staples, the detached soft tissue is typically moved back into its original position over the bone. The staple is then driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. A suture anchor is then deployed in the hole using an appropriate installation tool. This effectively locks the suture to the bone, with the free end(s) of the suture extending out of the bone. The free end(s) of the suture are passed through or around the soft tissue and are used to tie the soft tissue securely to the bone.

While current suture anchors are effective in anchoring soft tissue to bone, one drawback with current devices is that the suture and soft tissue attached thereto can slip or otherwise move while the suture anchor is being driven into the bone. Once the suture anchor has been driven into bone, the suture and the soft tissue cannot be adjusted to adjust the position of the soft tissue relative to the bone because the driven suture anchor holds the suture and soft tissue in place. The soft tissue may therefore not be in an optimal position to facilitate healing. Even if the suture and the soft tissue can be adjusted after the suture anchor has been driven into bone, tying the suture into a knot can cause the soft tissue to slip from an optimal position.

Another drawback with current devices is that the suture anchor must have a head with a length that is sufficient to withstand a torque applied thereto by a driver. As a result of the increased length, the suture anchor will typically extend at least partially into underlying soft cancellous bone in order to position the head beneath the outer surface of the bone. The bone-engaging portion of the suture anchor will thus be mostly disposed within and engaged with cancellous bone, rather than cortical bone. This is due to the fact that the cortical bone is only about 1 mm to 3 mm in length, and the driver head is often longer than 3 mm. Once implanted, tension applied to the anchor via the sutures can cause the anchor to migrate into the cortical bone and thus the head of the suture anchor can become proud, resulting in a weak fixation among other problems.

Accordingly, there remains a need for improved methods and devices for attaching soft tissue to bone.

SUMMARY OF THE INVENTION

In one embodiment, a suture anchor is provided that includes an elongate body having proximal and distal ends defining a longitudinal axis therebetween. The suture anchor also includes a plurality of bone-engaging surface features formed on at least a proximal portion of an external surface of the elongate body. The elongate body can have an external sidewall extending longitudinally between the proximal and distal ends of the elongate body. The sidewall can be configured to allow a suture to slide therealong when the elongate body is disposed within a bone hole with a first friction force between the suture and the sidewall being less than a second friction force between the suture and an internal surface of the bone hole. The sidewall can be planar, can be non-planar, can be free of bone-engaging surface features, and/or can extend along the external surface of the elongate body. The elongate body can be cannulated or non-cannulated.

The suture anchor can also include a first opening extending through the sidewall at a location proximal to a suture-seating member extending transverse to the longitudinal axis. The first opening can extend into an inner lumen extending through the elongate body. The suture anchor can further include a second opening extending through the sidewall at a location proximal to the suture-seating member. The second opening can also extend into the inner lumen of the suture anchor.

The plurality of bone-engaging surface features can have a variety of configurations and can be formed on various portions of the suture anchor. The plurality of bone-engaging surface features can extend from a proximal-most end of the elongate body and terminate proximal to a suture-seating member extending transverse to the longitudinal axis. The plurality of bone-engaging surface features can include ribs spaced longitudinally along the elongate body and extending a partial circumference around the elongate body. Terminal ends of each of the ribs can be adjacent to the sidewall.

The elongate body can have a variety of configurations and include a variety of features. The elongate body can, for example, include a cavity configured to receive a suture. The cavity can be formed in the elongate body between a suture-receiving opening formed in a distal end of the elongate body and a suture-seating member extending transverse to the longitudinal axis and positioned proximal to the suture-receiving opening. For another example, a distal-most end of the elongate body can include opposed arms having suture-grasping members formed on opposed inner surfaces thereof. For yet another example, the elongate body can have an inner lumen extending therethrough, and a proximal portion of the inner lumen can have an asymmetrical cross-sectional shape configured to receive a driver tool therein. For still another example, the elongate body can include a cut-out formed in an outer surface thereof opposite to the sidewall. The cut-out can extend proximally from a distal-most end of the suture anchor. A suture-seating member extending transverse to the longitudinal axis and positioned proximal to a suture-receiving opening formed in a distal end of the elongate body can be positioned distal of a proximal end of the cut-out.

At least one suture can be coupled to the suture anchor. For example, a suture can be coupled to the suture anchor and can have a first portion extending along the elongate body, a second portion extending along the sidewall, and a third portion between the first and second portions extending around the distal end of the elongate body. The suture anchor can include a first opening extending through the sidewall r, the first opening extending through the elongate body, and the first portion of the suture extending through the inner lumen. A second suture can be coupled to the suture anchor and can have first and second portions extending through the inner lumen and a third portion between the first and second portions extending through the first opening.

The suture anchor can include a suture-receiving opening formed in a distal-most end of the elongate body, and a suture-seating member extending transverse to the longitudinal axis and positioned proximal to the suture-receiving opening. The suture-receiving opening can have a variety of configurations, such as being an elongate slot formed in a distal end of the elongate body.

In another embodiment, a suture anchor is provided that includes a cannulated elongate body having an inner lumen and having a plurality of bone-engaging surface features formed on a first portion of an external surface of the elongate body, and a sidewall extending longitudinally along a second portion of the external surface of the elongate body. When the suture anchor is disposed within a bone hole and the plurality of bone-engaging surface features are in engagement with an internal surface of the bone hole, the suture anchor can have a delivery orientation in which a suture positioned to extend through the inner lumen and along the planar sidewall is slidable along the planar sidewall with a first friction force between the suture and the sidewall that is less than a second friction force between the suture and the internal surface of the bone hole, and a locked orientation, rotatably offset from the delivery orientation, in which the suture is positioned within the bone hole between the plurality of bone-engaging surface features and the internal surface of the bone hole. With the suture anchor in the delivery orientation, the suture positioned to extend through the inner lumen and along the sidewall can be slidable within the inner lumen. The suture anchor can be configured to have the delivery and locked orientations when the suture anchor is completely disposed within the bone hole such that a proximal-most end of the elongate body does not extend proximally beyond a proximal-most end of the bone hole.

The suture anchor can vary in any number of ways. For example, the first and second portions can be on opposed sides radially around the elongate body. For another example, a proximal portion of the elongate body can include the bone-engaging surface features and the planar sidewall at a same axial position longitudinally along the elongate body.

In another aspect, an apparatus for anchoring tissue to bone is provided that includes a suture anchor and a driver. The suture anchor has proximal and distal ends and, a sidewall formed on an external surface thereof and extending between the proximal and distal ends. The sidewall can be configured to allow a suture to slide therealong when the suture anchor is disposed within a bone hole with a first friction force between the suture and the sidewall being less than a second friction force between the suture and an internal surface of the bone hole. The driver has an elongate shaft and a distal tip configured to mate with a proximal portion of the suture anchor. The distal tip is configured to align with the sidewall in a predetermined orientation. The driver has a suture alignment guide formed thereon and axially aligned with the sidewall on the distal tip to thereby align a suture extending longitudinally along the elongate shaft with the sidewall on the suture anchor.

At least one suture can be coupled to the suture anchor and the driver. For example, a suture can be coupled to the suture anchor and the driver, with a first portion extending longitudinally along the anchor, and a second portion extending along the planar sidewall, extending longitudinally along the anchor, and engaging the suture alignment guide. A second suture can be coupled to the suture anchor and the driver, with a first portion extending longitudinally along the anchor and a second portion extending through a cannulated interior of the driver. The suture can be slidably movable relative to the suture anchor and the driver, and the second suture can not be slidably movable relative to the suture anchor and the driver.

The suture alignment guide can have a variety of configurations. In one embodiment, the suture alignment guide can include a slot formed in the driver configured to receive and engage a suture.

The anchor can include a suture-seating member extending across an inner lumen extending between the proximal and distal ends of the anchor. The suture-seating member can be positioned proximal to a suture-receiving cut-out formed in a distal end of the suture anchor.

In another aspect, a method for anchoring suture to bone is provided that includes inserting a suture anchor with a suture coupled thereto into a bone hole in bone such that a proximal end of the suture anchor is positioned substantially flush or sub-flush with a proximal opening of the bone hole, and a plurality of bone-engaging surface features on an external surface of the suture anchor engage the bone hole to prevent removal of the suture anchor from the bone hole. The external surface of the suture anchor can be planar, and, after the suture anchor is inserted into the bone hole, the suture can extend through an inner lumen of the suture anchor, around a suture-seating member extending across the inner lumen, and along the external planar surface of the suture anchor. After the suture anchor is inserted into the bone hole, a suture-receiving space can extend along the suture anchor between the bone surface defining the bone hole and the external surface of the suture anchor free of the bone-engaging surface features. After inserting the suture anchor, tension can be applied to the suture such that the suture slides between a bone surface defining the bone hole and an external surface of the suture anchor free of the plurality of bone-engaging surface features. After applying the tension, the suture anchor can be rotated within the bone hole such that the suture becomes engaged between the bone-engaging surface features on the suture anchor and the bone surface of the bone hole. When the suture anchor is rotated, a first friction force between the suture and the external surface of the suture anchor free of the plurality of bone-engaging surface features can be less than a second friction force between the suture and the bone surface of the bone hole.

Applying tension to the suture anchor can be effective to pull tissue coupled to the suture toward the bone hole. The tension can be applied, for example, by pulling the suture through a guide member formed on a driver coupled to the suture anchor. The guide member can maintain axial alignment of the suture with the external surface of the suture anchor free of the bone-engaging surface features.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
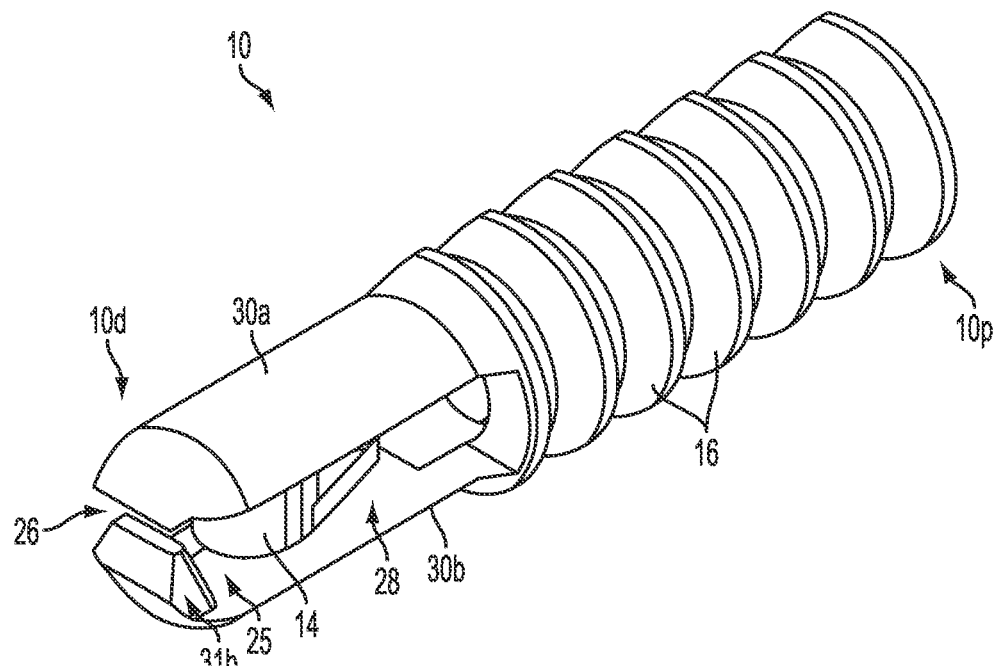
FIG. 1 is a perspective view of one embodiment of a suture anchor.
Figure 2:
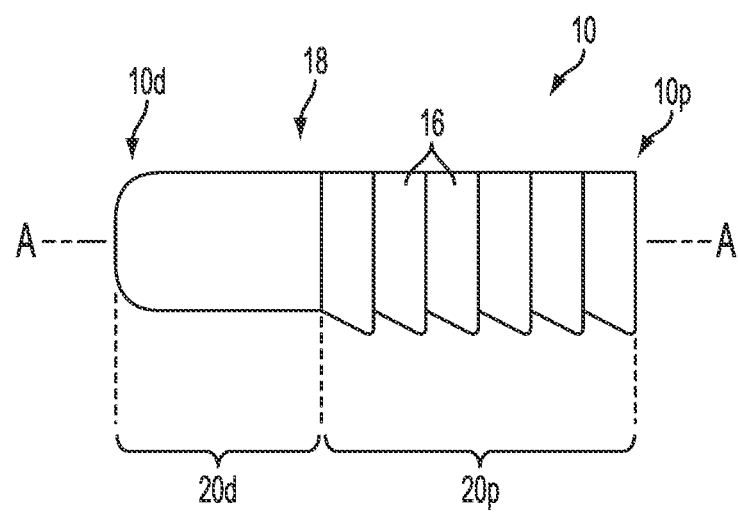
FIG. 2 is a side view of the suture anchor of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for anchoring soft tissue to bone. In general, the methods and devices can allow soft tissue to be secured to bone using a suture coupled to a suture anchor without knotting or otherwise tying the suture to secure the soft tissue in place relative to the bone. Exemplary suture anchor drivers and suture anchor threaders are also provided that can be used with the various methods and devices disclosed herein, or with other methods and devices known in the art. A person skilled in the art will appreciate that while methods and devices are disclosed herein for anchoring soft tissue to bone, the methods and devices can be used in a variety of other medical procedures for anchoring various objects to one another.

In an exemplary embodiment, a suture anchor is provided that includes one or more bone-engaging surfaces features and an external sidewall. The external sidewall can allow a suture coupled to the suture anchor and located between the anchor and bone to be movable relative to the suture anchor, even when the suture anchor is partially or fully disposed within a bone hole. Tension of the suture can therefore be precisely adjusted to adjust positioning of a soft tissue coupled thereto. In other words, the suture anchor can facilitate adjustment of suture/tissue tension by allowing suture/tissue tension to be adjusted independent of the suture anchor's insertion depth within a bone hole. The suture anchor allows for adjustment of suture/tissue tension both before and after the suture anchor has been fully inserted into the bone hole with the anchor's proximal end being substantially flush or sub-flush with a proximal opening of the bone hole. In other words, the suture anchor can allow suture/tissue tension to be adjusted after the suture anchor has been inserted any depth into a bone hole, thereby facilitating healing by allowing for more precise positioning of the soft tissue relative to the bone, e.g., to increase contact between the soft tissue and the bone when the soft tissue is in its anchored position. The suture anchor can also eliminate the need for a driver head formed on the suture anchor, and as a result the entire length of the suture anchor can be configured to be fully engaged through the thickness of hard cortical bone, thus optimizing cortical bone fixation to provide a more secure fixation. This can help prevent migration of the suture anchor.

FIGS. 1-8 illustrate one exemplary embodiment of a suture anchor 10 configured to anchor soft tissue to bone. As in the illustrated embodiment, the anchor can be a unitary element. As also in the illustrated embodiment, the anchor 10 can include a generally elongate body having proximal and distal ends 10p, 10d with an inner lumen 12 extending therebetween. The anchor 10 can include a suture-seating member 14 disposed within the inner lumen 12 adjacent to the distal end 10d of the anchor 10. Generally, the suture-seating member 14 can be configured to seat a suture extending at least partially through the inner lumen 12 so as to help securely couple the suture to the anchor 10. The anchor 10 can also include at least one bone-engaging surface feature 16 configured to engage bone. The at least one bone-engaging surface feature 16 can be formed on at least a portion of an external surface of the elongate body, e.g., in a proximal portion 20p of the elongate body. A distal portion 20d of the elongate body can be free of bone-engaging surface features. The anchor 10 can also include a planar sidewall 18 extending longitudinally between the proximal and distal ends 10p, 10d of the elongate body to define a planar or flat external surface thereof. The planar sidewall 18 can be smooth. A person skilled in the art will appreciate that the sidewall 20 may not be precisely planar, flat, or smooth because of machining tolerances. As discussed further below, the at least one bone-engaging surface feature 16 and the planar sidewall 18 can cooperate to selectively allow a suture extending through the inner lumen 12 of the anchor 10 to be adjustable relative to the elongate body, even when the anchor 10 is partially or fully disposed in a bone tunnel, and to allow the suture to be locked in a fixed position relative to the elongate body when the anchor 10 is partially or fully disposed in the bone tunnel.

A person skilled in the art will appreciate that when the anchor 10 is partially disposed within the bone tunnel, the anchor's distal-most end is disposed in the bone tunnel and the anchor's proximal-most end is proximal to a proximal-most end of the bone tunnel. A person skilled in the art will also appreciate that when the anchor 10 is fully disposed within the bone tunnel, the anchor's distal-most end is disposed in the bone tunnel and the anchor's proximal-most end is substantially flush or sub-flush with the proximal-most end of the bone tunnel, e.g., is aligned with or is located distal to the proximal-most end of the bone tunnel.

The anchor 10 can be formed from a variety of materials. In an exemplary embodiment, the material can have physical properties that are sufficient to allow a driver to be inserted into the inner lumen 12 of the anchor 10 and to be used to drive the anchor 10 into bone without damaging the anchor 10. The properties of the material will depend on the particular configuration of the anchor 10. For non-limiting example, the inner lumen 12 of the anchor 10 can have a length that maximizes the torque strength of the anchor 10 as well as the amount of surface contact between a driver and the anchor 10, thus allowing weaker materials, such as bioabsorbable and/or osteoconductive materials to be used. For another non-limiting example, the material that forms at least an external surface of the sidewall 18 can be configured to provide a smaller frictional force between the sidewall and a suture than a bone surface and the suture, which can help position the suture within the bone hole, as discussed further below. For yet another non-limiting example, the material that forms at least an external surface of the sidewall 18 and the material that forms the at least one bone-engaging surface feature 16 can be configured to provide a smaller frictional force between the sidewall and a suture than the at least one bone-engaging surface feature 16 and the suture, which can help position the suture within the bone hole, as discussed further below. A person skilled in the art will appreciate that a variety of other materials, including plastics and metals, can be used to form the suture anchor 10.

The elongate body of the suture anchor 10 can have a variety of configurations, shapes, and sizes. In an exemplary embodiment, the elongate body can be configured to be implanted within a bone tunnel formed in bone. The elongate body can have a size and shape that allows it to be fully engaged through the thickness of the cortical bone. As in the illustrated embodiment, the body can have a generally elongate shape with a blunt or rounded distal end 10d, which can facilitate introduction of the anchor 10 into a bone tunnel. The proximal end 10p of the body can be head-free, as the cannulated configuration of the body allows a driver to be inserted into the inner lumen 12 to drive the suture anchor 10 into bone.

The at least one bone-engaging surface feature 16 of the suture anchor 10 can also have a variety of configurations, shapes, and sizes. While various surface features can be used, such as teeth, threads, barbs, protrusions, etc., as in the illustrated exemplary embodiment, the elongate body can include a surface feature 16 in the form of one or more ridges, flanges, or ribs extending therearound and conducive to being pushed into bone hole without rotation of the anchor 10. In the illustrated embodiment, the anchor 10 includes a plurality of bone-engaging surface features 16. Although the anchor 10 includes seven bone-engaging surface features 16 in this illustrated embodiment, the anchor 10 can include any number of bone-engaging surface features 16. Providing multiple bone-engaging surface features 16, rather than only one bone-engaging surface feature 16, can facilitate more secure disposal of the anchor 10 at least partially within a bone tunnel and help prevent migration of the anchor 10 therein, which can facilitate proper healing. Providing multiple bone-engaging surface features 16 can also help the anchor 10 more securely hold or pinch a suture between the anchor 10 and bone, as discussed further below, which can help hold a soft tissue attached to the suture in a consistent position relative to the bone to facilitate proper healing.

As mentioned above, the at least one bone-engaging surface feature 16 can be located entirely in the proximal portion 20p of the elongate body. The elongate body of the anchor 10 can therefore have a proximal region configured to penetrate into and/or form grooves in a bone wall defining a bone tunnel and a distal region configured to be disposed within the bone tunnel without penetrating into and/or forming grooves in the bone wall of the bone tunnel. In an exemplary embodiment, the at least one bone-engaging surface feature 16 can extend from a proximal-most end of the anchor 10 to a location proximal to the distal end 10d of the anchor 10. The particular location at which the at least one bone-engaging surface feature 16 terminate can vary depending on the particular configuration of the anchor 10. As in the illustrated embodiment, the at least one bone-engaging surface feature 16 can terminate proximal to a proximal-most end of the suture-seating member 14. As discussed in more detail below, the anchor 10 can include opposed cut-outs formed in the distal portion 10d thereof, and the at least one bone-engaging surface feature 16 can terminate just proximal to a proximal end of the cut-outs.

Figure 3:
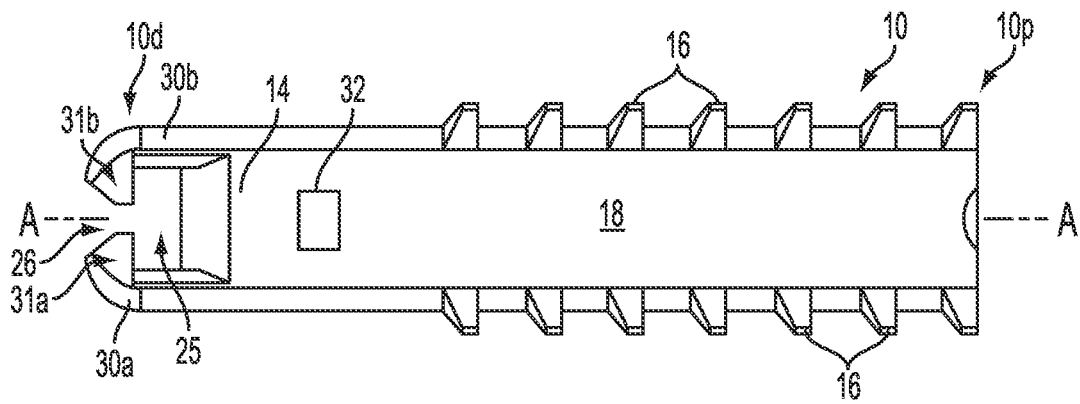
FIG. 3 is a side view of the suture anchor of FIG. 1 facing a planar sidewall of the suture anchor.
Figure 4:
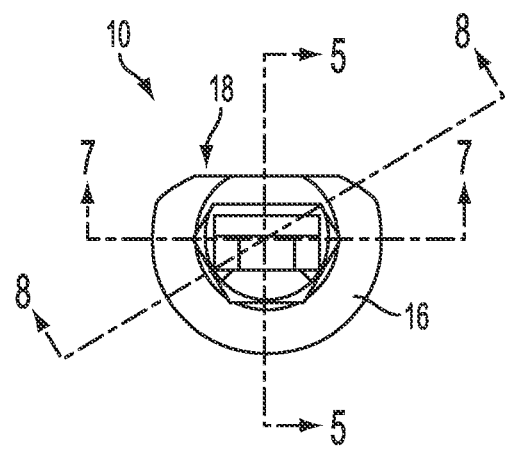
FIG. 4 is a proximal view of the suture anchor of FIG. 1.
Figure 10:
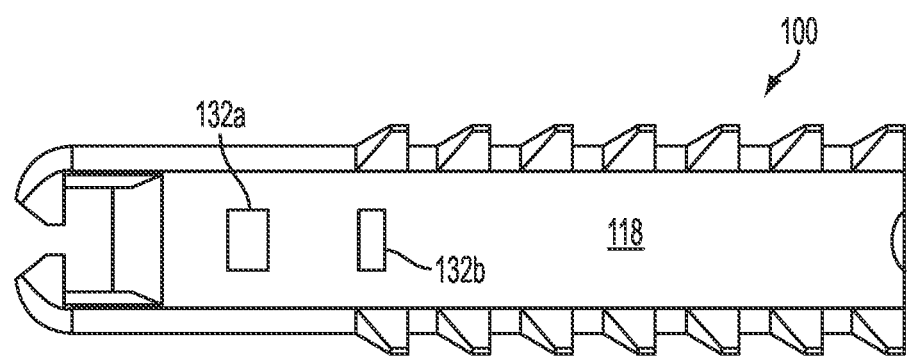
FIG. 10 is a side view of another embodiment of a suture anchor facing a planar sidewall of the suture anchor.

The planar sidewall 18 can prevent the at least one bone-engaging surface feature 16 from extending fully radially around the anchor 10 because the planar sidewall 18 can extend along an entire longitudinal length of the elongate body in at least the proximal portion 20p of the anchor 10 that also includes the bone-engaging surface features 16 along an entire longitudinal length thereof. The bone-engaging surface features 16 can therefore extend radially around a partial perimeter or circumference of the external surface of the anchor 10. With the bone-engaging surface features 16 being ridges, as in the illustrated embodiment, each of the individual ridges can have terminal ends abutting the planar sidewall, as shown in FIG. 3. The anchor 10 can therefore include a "bald spot" in at least the proximal portion thereof due to the planar sidewall. As in the illustrated embodiment, the external surface of the elongate body including the at least one bone-engaging surface feature 16 can be rounded such that each of the bone-engaging surface features 16 can be substantially u-shaped or substantially c-shaped, as shown in FIG. 4. The elongate body of the anchor 10 can therefore have a substantially D-shaped cross-sectional shape in at least the proximal portion 20p thereof, as also shown in FIG. 4. The rounded shape of the at least one bone-engaging surface feature 16 can facilitate secure disposal of the elongate body within a bone tunnel having rounded walls, e.g., a cylindrical-shaped bone tunnel. In this way, as shown in FIG. 10 and as discussed further below, when the anchor 10 is disposed within a bone tunnel 22, the elongate body of the anchor 10 can have one side thereof configured to engage a bone wall 24 defining a bone tunnel, e.g., a side including the one or more bone-engaging surface features 16, and an opposite side thereof, e.g., a side including the planar sidewall 18, spaced a distance D away from the bone surface or wall 24. The distance D can be equal to or greater than a diameter of a suture extending along the planar sidewall 18 so as to allow the suture to slidably move within the gap between the sidewall 18 and the bone wall 24. The distance D can be less than the diameter of the suture extending along the planar sidewall 18 and still allow the suture to slidably move within the gap between the sidewall 18 and the bone wall 24, such as if the suture is compressible. The suture can have any size, e.g., #2 suture, as appropriate for the particular procedure in which it is used. Similarly, an inner diameter D2 of the bone tunnel can be less than a minor diameter D3 of the anchor and slightly larger than a major diameter D4 of the anchor 10.

The suture-seating member 14 can also have a variety of configurations, shapes, and sizes, but in an exemplary embodiment, it is adapted to engage one or more sutures that extend at least partially through the inner lumen 12 of the anchor 10. As shown in FIGS. 1, 3, 5, and 7, the suture-seating member 14 can be in the form of a post that extends transversely across the inner lumen 12 relative to a longitudinal axis A of the anchor 10 and that extends between opposed inner sidewalls of the anchor 10. The angular orientation of the suture-seating member 14 relative to the longitudinal axis A of the anchor 10 can vary, but in an exemplary embodiment the suture-seating member 14 can extend substantially perpendicular to the longitudinal axis A. The location of the suture-seating member 14 within the inner lumen 12 of the anchor 10 can also vary, but in an exemplary embodiment, the suture-seating member 14 can be positioned at or adjacent to the distal end 10d of the suture anchor 10. As in the illustrated embodiment, the suture-seating member 14 can be located just proximal to a distal-most end of the suture anchor 10 so as to define a cavity 25 formed in the elongate body between the suture-seating member 14 and a suture-receiving opening 26 formed in the distal-most end of the suture anchor 10. This recessed configuration of the suture-seating member 14 can allow for one or more sutures disposed around the suture-seating member 14 to sit substantially flush or sub-flush with the distal end 10d of the suture anchor 10 such that the suture(s) will not interfere with insertion of the suture anchor 10 into bone. The suture-receiving opening 26 can also allow a suture to be moved therethrough to help couple the suture to the anchor 10. The suture-receiving opening 26 is shown in the illustrated embodiment as an elongate slot, but the suture-receiving opening 26 can have other shapes. A person skilled in the art will appreciate that the suture-seating member 14 can be integrally formed with the suture anchor 10, i.e., the suture anchor 10 and suture-seating member 14 can be molded as a single unit or formed from a single piece of material, or the suture-seating member 14 can be fixedly or removably mated to the suture anchor 10. In an exemplary embodiment, the suture-seating member 14 can be at a fixed location along the longitudinal length of the anchor 10 such that the suture-seating member 14 is non-movable relative to a remainder of the anchor 10. Such a fixed position can help more one or more sutures engaged with the suture-seating member 14 to be more predictably moved relative to the anchor 10 and secured in a selected position relative thereto.

In another embodiment, rather than having a fixed suture-seating member 14, a suture anchor can include a suture-seating member that is rotatably disposed therein. Such a configuration can allow for suture slidability, providing a pulley system to facilitate longitudinal movement of a suture through the inner lumen of the suture anchor. In particular, one or more terminal ends of one or more sutures disposed around the suture-seating member can be pulled to slide the suture(s) longitudinally within the inner lumen of the suture anchor, and the suture-seating member can rotate to facilitate such longitudinal movement. Exemplary embodiments of a rotatable suture-seating member are discussed in further detail in U.S. Patent Publication No. 2008/0147063 entitled "Cannulated Suture Anchor" filed Nov. 1, 2006, which is hereby incorporated by reference in its entirety.

Figure 7:
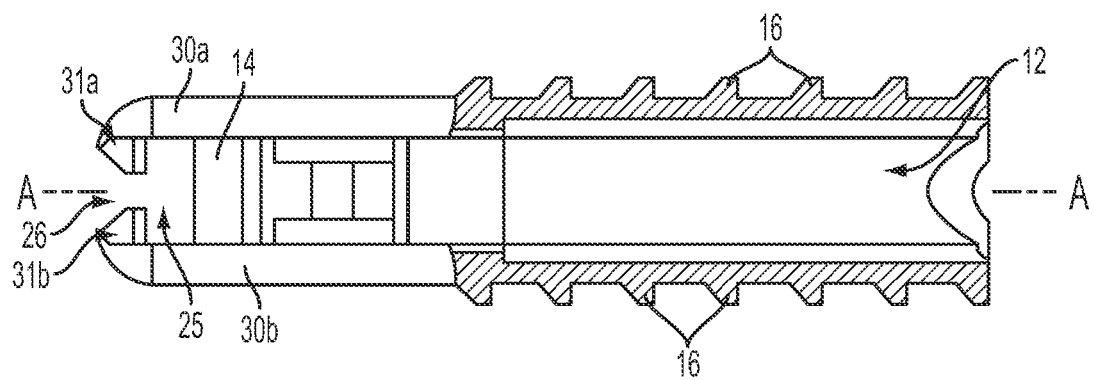
FIG. 7 is another cross-sectional view of the suture anchor of FIG. 1 perpendicular to the cross-sectional view of FIG. 5.
Figure 8:
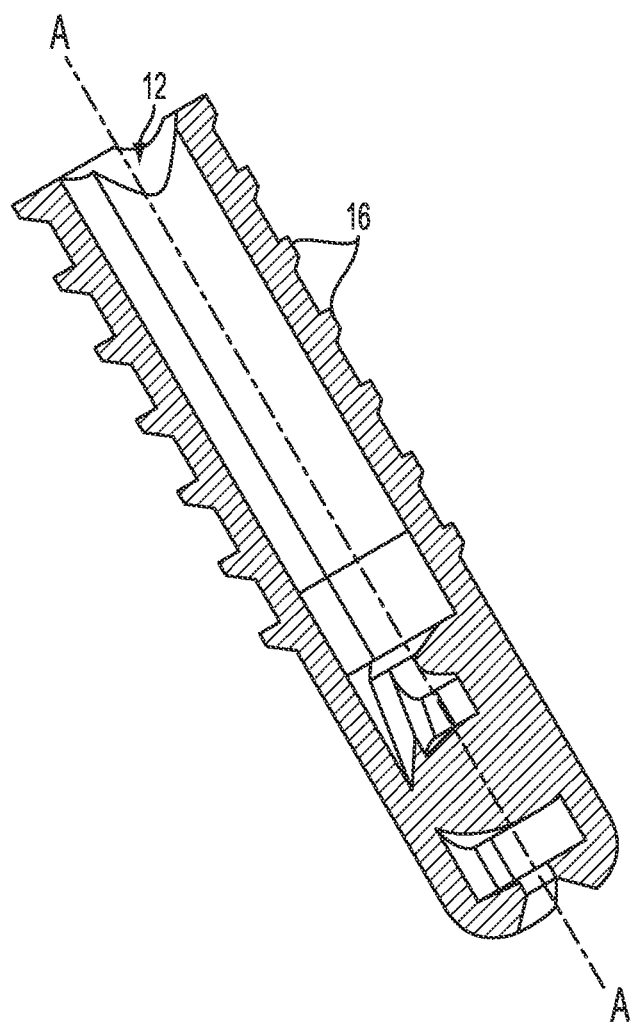
FIG. 8 is another cross-sectional view of the suture anchor of FIG. 1.

As shown in FIG. 1, the anchor 10 can include one or more cut-outs 28 formed in a sidewall thereof adjacent to the suture-seating member 14, which can facilitate positioning of one or more sutures around the suture-seating member 14. As in the illustrated embodiment, the anchor 10 can include one cut-out 28 that begins just proximal to the location of the suture-seating member 14, and that extends around the distal end 10b of the suture anchor 10 such that the suture anchor 10 includes a cut-out or opening formed on one side of the suture-seating member 14 and a distal cut-out that defines the suture-seating groove 26 configured to seat one or more sutures. The side of the anchor 10 opposite the cut-out 28 can include the planar sidewall 18. The cut-out 28 can also define opposed distal arms 30a, 30b on the anchor 10, as shown in FIGS. 1, 3, and 7, that are spaced a distance apart from one another and that have the suture-seating member 14 extending therebetween. Distal-most ends of the arms 30a, 30b can have the suture-receiving opening 26 formed therebetween. The distal arms 30a, 30b can have suture-grasping members 31a, 31b formed on opposed inner surfaces thereof. The suture-grasping members 31a, 31b can be configured to help prevent a suture positioned within the cavity 25 from slipping distally beyond the anchor 10. Although, as mentioned above, force can be applied to a suture positioned within the cavity 25 to pull, snap, or push it through the suture-receiving opening 26 to help desirably position the suture, e.g., when loading a tension suture to extend along the planar sidewall 18. The suture-grasping members 31a, 31b can be orientated so as to form the suture-receiving opening 26 as an elongate slot having a longitudinal axis substantially perpendicular to a longitudinal axis of the planar sidewall 18, e.g., to the axis A of the anchor 10. In this way, a suture pulled, snapped, or pushed through the suture-receiving opening 26 can be aligned to smoothly extend along the sidewall 18.

A person skilled in the art will appreciate that the particular location and configuration of the cut-out 28 can define the particular location and configuration of the suture-seating member 14, as the cut-out 28 can be formed during manufacturing to create the suture-seating member 14. Alternatively, the particular location and configuration of the opposed arms 30a, 30b can define the particular location and configuration of the cut-out 28, as the shape and size of the arms 30a, 30b defines the shape and size of the cut-out 28. The location of the suture-seating member 14 relative to the cut-out 28 and/or arms 30a, 30b will also define the configuration of the distal end of the suture anchor 10, and whether the suture anchor 10 includes the distal groove 26 configured to seat one or more sutures.

Figure 5:
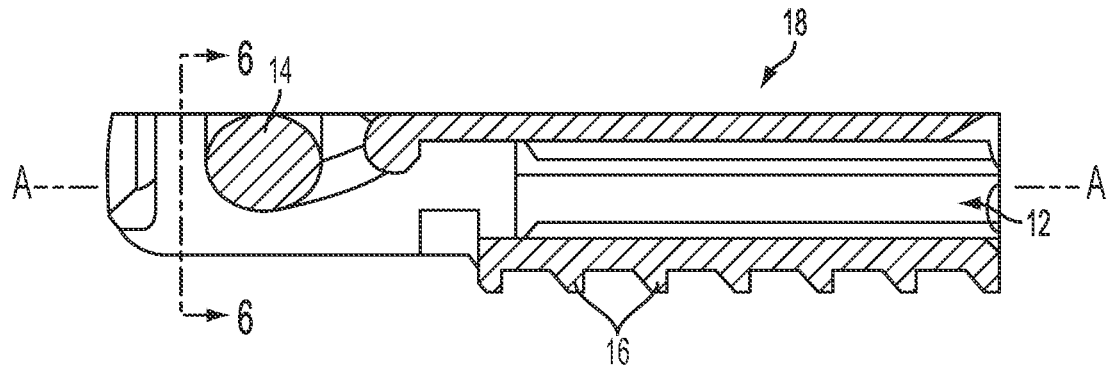
FIG. 5 is a cross-sectional view of the suture anchor of FIG. 1.
Figure 6:
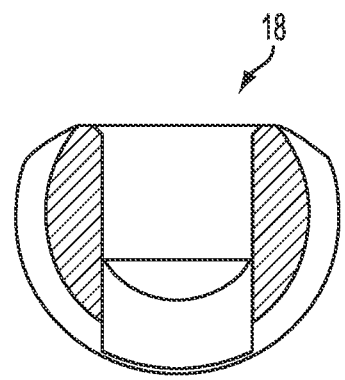
FIG. 6 is a cross-sectional view of a distal portion of the suture anchor of FIG. 1.

Proximal to the suture-seating member 16, the anchor 10 can include at least one hole or opening 32 extending through the planar sidewall 18 of the anchor 10, as shown FIG. 3. In this illustrated embodiment, the anchor 10 includes one opening 32. The opening 32 is shown as a rectangular opening, but the opening 32 can have any shape. As in the illustrated embodiment, a proximal-most end of the suture-seating member 14 can define a distal-most end of the opening 32 such that the opening 32 is located entirely proximal to the suture-seating member 14 and such that the suture-seating member 14 and the opening 32 are immediately adjacent to one another. Such positioning can facilitate engaging a suture with the suture-seating member 14 and passing the suture through the opening 32, as discussed further below. As shown in FIGS. 1 and 5, the suture-engaging member 14 can be configured to slope proximally toward the opening 32. Such a slope can also facilitate engaging a suture with the suture-seating member 14 and passing the suture through the opening 32.

The location of the opening 32 along the longitudinal length of the anchor 10 can vary, but as in the illustrated embodiment, the opening 32 can be located entirely in the distal portion 20d of the anchor 10, e.g., located distal to a distal-most end of the at least one bone-engaging surface feature 16. Being located entirely in the distal portion 20 of the anchor 10 can help prevent a suture extending through the opening 32 from contacting the at least one bone-engaging surface feature 16. If the anchor 10 includes a plurality of openings extending through the planar sidewall 18, at least one of the openings, e.g., a distal-most one of the openings, can be located entirely within the distal portion 20d, and a remainder of the openings can be variously located entirely within the distal portion 20d, entirely within the proximal portion 20p, or partially within each of the distal and proximal portions 20d, 20p. FIG. 10 illustrates an exemplary embodiment of a suture anchor 100 configured similar to the anchor 10 of FIG. 1 but including a plurality of openings 132a, 132b formed through a planar sidewall 118 of the anchor 100.

Referring again to the anchor embodiment of FIG. 1, as mentioned above, the anchor 10 can be configured to have one or more sutures coupled thereto and at least partially extending through the inner lumen 12 thereof. In an exemplary embodiment, two sutures can be coupled to the anchor 10, namely a first, tension suture to couple the anchor 10 to soft tissue, and a second, stay suture to facilitate holding and manipulating the anchor 10 during a procedure implanting the anchor 10 within a body of a patient. A person skilled in the art will appreciate that the tension suture and the stay suture can each include any number of individual suture strands, same or different from one another.

Figure 11:
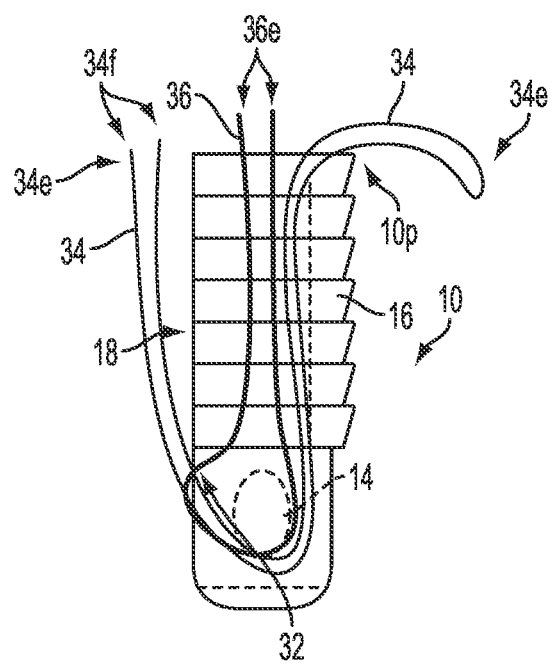
FIG. 11 is a side, partially transparent view of the suture anchor of FIG. 1 having two sutures coupled thereto.

As shown in FIG. 11, the anchor 10 can be configured to simultaneously couple to a tension suture 34 configured to couple to soft tissue, e.g., by tying, and to a stay suture 36. Regarding the tension suture 34, the suture-seating member 14 can be configured to receive the tension suture 34 therearound such that the tension suture 34 can extend through the inner lumen 12 and extend around the suture-seating member 14 so as to be located partially within the anchor 10 and partially external to the anchor 10. More particularly, the suture-seating member 14 can be configured to allow a first length of the tension suture 34 to extend through the inner lumen 12 and out of the proximal end 10p of the suture anchor 10, a second length of the tension suture 34 to extend along the planar sidewall 18 external to the suture anchor 10 and proximally beyond the proximal end 10p of the suture anchor 10, and a third length of the tension suture 34 between the first and second lengths to be bent or curved around the suture-seating member 14. The tension suture 34 can thus extend along the planar sidewall 18 and bypass the opening 32 formed therethrough.

As shown in FIG. 11, ends 34e of the tension suture 34 can be located proximal to the proximal end 10p of the anchor 10. One or both of the ends 34e can be manipulated, e.g., by hand, by surgical tool, etc., to slidably move the tension suture 34 within the inner lumen 12 and along the sidewall 18. As discussed further below, this slidable movement can allow the tension suture 34, and hence also any soft tissue coupled thereto, to be adjusted relative to the anchor 10, and to a bone tunnel in which the anchor 10 is at least partially disposed, before and/or after any one or more of the one or more bone-engaging surfaces feature 16 has engaged bone to position the soft tissue in a desirable position relative to the bone for healing.

Regarding the stay suture 36, the suture-seating member 14 can be configured to receive the stay suture 36 therearound such that the stay suture 36 can extend through the inner lumen 12 and extend around the suture-seating member 14 so as to be substantially located within the anchor 10. The opening 32 can be configured to cooperate with the suture-seating member 14 to allow the stay suture 36 to reenter the inner lumen 12 after being bent or curved around the suture-seating member 14. More particularly, the suture-seating member 14 can be configured to allow a first length of the stay suture 36 to extend through the inner lumen 12 and out of the proximal end 10p of the suture anchor 10, a second length of the stay suture 36 to extend along the planar sidewall 18 external to the suture anchor 10 before the stay suture 36 reenters the anchor 10 through the opening 32, a third length of the stay suture 36 proximal to the opening 21 extending through the inner lumen 12 and proximally beyond the proximal end 10p of the suture anchor 10, and a fourth length between the first and second lengths to be bent or curved around the suture-seating member 14. As shown in FIG. 11, ends 36e of the stay suture 36 can be located proximal to the proximal end 10p of the anchor 10. The ends 36e, as discussed further below, can be coupled to a driver to facilitate implantation of the anchor 10 within a body of a patient.

Although the tension suture 34 is illustrated in FIG. 11 as being doubled-over with both its free ends 34f together, the tension suture 34 can be folded over more than twice or can be non-folded such that its free ends 34f are separate, e.g., with one free end 34f being at a terminal end of the suture's first length and the other free end 34f being at a terminal end of the suture's second length. Similarly, the stay suture 36 is shown in FIG. 11 as a non-folded single strand, but the stay suture 36 can be folded any number of times. Additionally, although only one tension suture 34 and one stay suture 36 are illustrated in FIG. 11, one or more tension sutures and one or more stay sutures can be simultaneously coupled to the anchor 10 with the one or more tension sutures each being positioned with a partial length thereof within the inner lumen 12 and another partial length thereof extending along the sidewall 18 and with the one or more stay sutures passing through the opening 32.

If a suture anchor includes multiple openings formed through a planar sidewall thereof, at least one suture can be coupled to the anchor without being bent or curved around a suture-seating member of the anchor. In other words, at least one suture coupled to the anchor can be located entirely proximal to the suture-seating member. Coupling the stay suture to the anchor with the stay suture being positioned entirely proximal to the suture-seating member can help reduce interference of the stay suture with adjustment or tensioning of a tension suture also coupled to the anchor.

Figure 12:
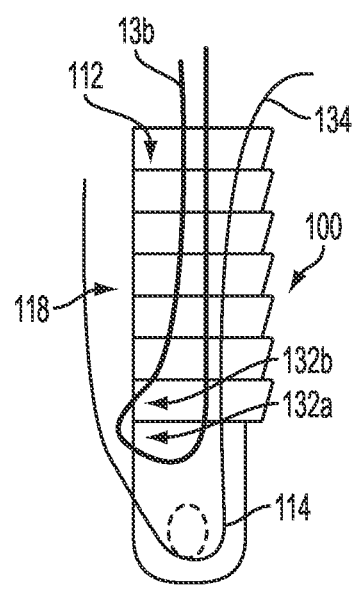
FIG. 12 is a side, partially transparent view of the suture anchor of FIG. 10 having two sutures coupled thereto.

FIG. 12 illustrates a tension suture 134 and a stay suture 136 coupled to the anchor 100 of FIG. 10 that includes first and second openings 132a, 132b formed through the planar sidewall 118 thereof. The tension suture 134 as shown can be coupled to the anchor 100 similar to the coupling of the tension suture 34 to the anchor 10 of FIG. 11. The stay suture 136 can be coupled to the anchor 100 without being bent or curved around a suture-seating member 114 of the anchor 100 by extending through an inner lumen 112 of the anchor 100, passing out of the anchor 100 through the first opening 132a, and passing back into the inner lumen 112 through the second opening 132b. The tension suture 134 and the stay suture 136 are each illustrated in this embodiment as being non-folded, although, as mentioned above, one or both can be folded and one or both can include multiple strands of individual suture.

The anchor 10 of FIG. 1 and the anchor 100 of FIG. 10 are each cannulated. However, a suture anchor can be non-cannulated. A non-cannulated suture anchor can couple to a suture in a variety of ways, such as by having the suture extend along external surfaces thereof, e.g., a first length of the suture extending along a side of the anchor including one or more bone-engaging surface features, a second length of the suture extending along an external sidewall thereof, and a third length of the suture between the first and second length extending around a distal end of the anchor. A distal end of a non-cannulated suture anchor can optionally include a suture-seating member and/or a suture-receiving opening to help couple a suture to the non-cannulated anchor. A proximal end of a non-cannulated suture anchor can optionally include a bore formed therein configured to help seat a distal end of a driver.

The sidewall 18 of the anchor 10 of FIG. 1 is planar, as is the sidewall 118 of the anchor 100 of FIG. 10. However, a suture anchor can include an external, non-planar sidewall extending longitudinally between proximal and distal ends of the anchor's elongate body. The non-planar sidewall can otherwise be configured similar to the planar sidewalls discussed herein, e.g., be smooth, include a texture, have a friction force relative to a suture different from a friction force between the suture and bone, have a friction force relative to a suture different from a friction force between the suture and one or more bone-engaging surface features opposite the sidewall, etc. In one exemplary embodiment, the non-planar sidewall can include one or more surface features configured to engage bone and/or to help hold a suture thereagainst before the anchor is rotated. Non-limiting examples of such sidewall surface features include a rough or bumpy textured surface, a minor bone-engaging surface feature such as a minor thread, a groove configured to seat a suture, one or more protrusions or rails configured to help direct a suture, etc., and combinations thereof.

Figure 13:
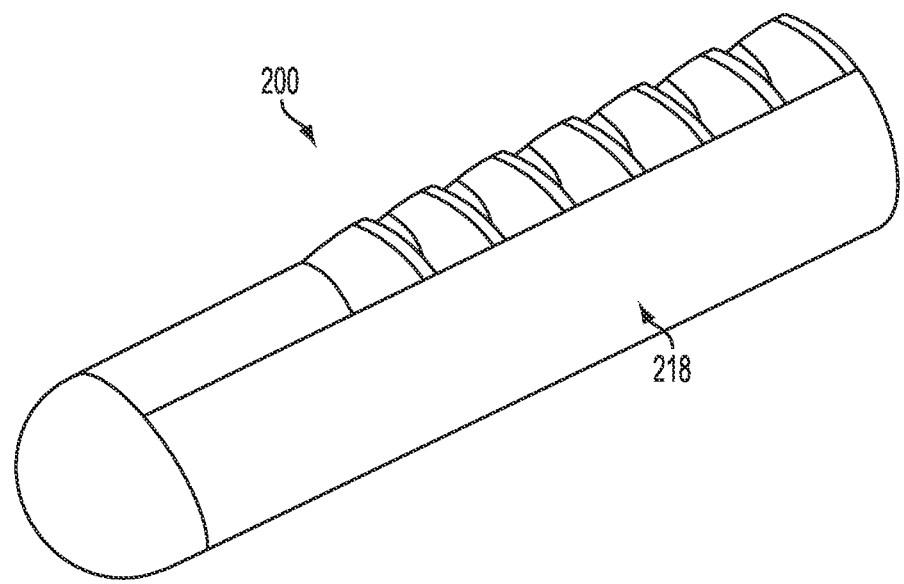
FIG. 13 is a perspective view of one embodiment of a suture anchor that includes a non-planar sidewall.
Figure 14:
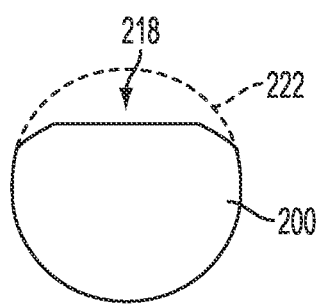
FIG. 14 is a proximal view of the suture anchor of FIG. 13 disposed in a bone hole.

FIGS. 13 and 14 illustrate an exemplary embodiment of a suture anchor 200 configured similar to the anchor 10 of FIG. 1 and the anchor 100 of FIG. 10 but including a non-planar sidewall 218 and being non-cannulated. A suture anchor can, however, be cannulated and include a non-planar sidewall or be non-cannulated and include a planar sidewall. The non-planar sidewall 218 can have a variety of shapes. An in this illustrated embodiment, the non-planar sidewall 218 can be radial, e.g., have a horizontal non-zero degree of curvature. A distal end of the anchor 200 in this illustrated embodiment does not include a suture-seating member or a suture-receiving opening, and a proximal end of the anchor 200 in this illustrated embodiment does not include a bore formed therein. FIG. 14 illustrates the anchor 200 disposed in a bone hole 222.

Figure 15:
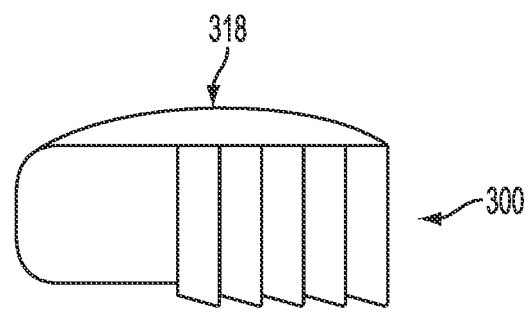
FIG. 15 a perspective view of another embodiment of a suture anchor that includes a non-planar sidewall.

FIG. 15 illustrates another exemplary embodiment of a suture anchor 300 configured similar to the anchor 10 of FIG. 1, the anchor 100 of FIG. 10, and the anchor 200 of FIG. 13 but including a non-planar sidewall 318. The anchor 300 in this illustrated embodiment is cannulated. The non-planar sidewall 318 in this illustrated embodiment is radial, e.g., has a horizontal non-zero degree of curvature and has a longitudinal or vertical non-zero degree of curvature.

Figure 9:
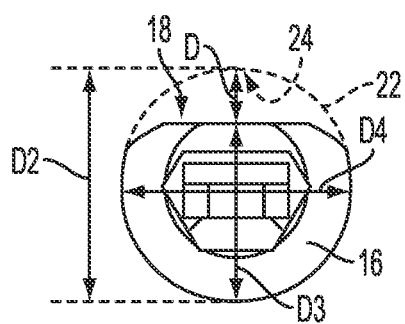
FIG. 9 is a proximal view of the suture anchor of FIG. 1 disposed in a bone hole.

As mentioned above, a suture anchor can be configured to be driven into bone with a driver at least partially inserted into an inner lumen of the anchor. Referring again to the anchor embodiment of FIG. 1, as shown in FIGS. 4, 7, and 9, the inner lumen 12 of the anchor 10 can be configured to receive a driver therein for driving the anchor 10 into bone. While various techniques can be used to facilitate engagement between the inner lumen 12 and a driver, in an exemplary embodiment at least a proximal portion of the inner lumen 12 can have an asymmetrical shape that complements a corresponding asymmetrical shape of a driver. The asymmetrical portion preferably extends along a substantial length of the inner lumen 12 so as to maximum surface contact between a driver and the suture anchor. By way of non-limiting example, FIGS. 4, 7, and 9 illustrate an asymmetrical hexagonal cross-sectional shape, e.g., with reference to the FIG. 7 line shown in FIG. 4, formed in a proximal portion of the inner lumen 12 for receiving a driver having a corresponding hexagonal drive tip, as discussed further below. The hexagonal cross-section can extend from the proximal-most end of the anchor 10 and terminate just proximal to a proximal end of the cut-out 26.

While various drivers known in the art can be used to drive a suture anchor into bone, FIGS. 16-19 illustrate an exemplary embodiment of a driver 50 configured to drive a suture anchor into bone. As in this illustrated embodiment, the driver 50 can be cannulated such that one or more sutures, e.g., one or more stay sutures, coupled to the suture anchor can extend through an interior passageway thereof. The driver 50 can also be configured to allow one or more additional sutures, e.g., one or more tension sutures, coupled to the suture anchor to extend along an external surface of the driver 50. As shown, the driver 50 can include an elongate shaft 52 having an inserter 54 at a distal end 52d thereof and a handle 56 at a proximal end 52p thereof. The handle 56 and the inserter 54 can be non-removably fixed to the shaft 52 or they can be removably and replaceably coupled to the shaft 52. In an exemplary embodiment, the driver 50 is an integral unit in which the shaft 52, the inserter 54, and the handle 56 are non-removably coupled together. In another exemplary embodiment (not shown), a driver handle can be non-removably coupled to a driver shaft, and a driver inserter tip can be removably and replaceably coupled to the driver shaft. In this way, an driver inserter tip can be removed and replaced with another, different driver inserter tip to allow the driver to be used with differently sized suture anchors and/or suture anchors having differently shaped inner lumens.

The shaft 52, the inserter 54, and the handle 56 can each have a variety of configurations, sizes, and shapes. The shaft 52, shown in FIGS. 16 and 17, can be cannulated and can have an inner lumen 58 extending therethrough between proximal and distal ends 52p, 52d thereof. The shaft 52 in the illustrated embodiment has a substantially cylindrical shape, but the shaft 52 can have other shapes. The shaft's proximal end 52p can be configured to couple to a distal end 56d of the handle 56, and the shaft's distal end 52d can be configured to coupled to a proximal end 54p of the inserter 54. A window 60 can be formed through a sidewall of the shaft 52 in a distal portion thereof. The window 60 can be configured to allow visualization of a suture disposed within the inner lumen 58 of the shaft 52. The window 60 can also be configured to allow a suture, e.g., a tension suture, disposed within the inner lumen 58 of the shaft 52 to exit therefrom.

The shaft 52 can have one or more depth markings 62 printed or otherwise formed on an external surface thereof. The depth marking(s) 62 can be configured to facilitate visual assessment of the shaft's location within a body of a patient. In an exemplary embodiment, as shown in FIGS. 16 and 17, the shaft 52 can include a proximal depth marking 62 near the handle 56 and a distal depth marking 62 near the inserter 54.

Figure 16:
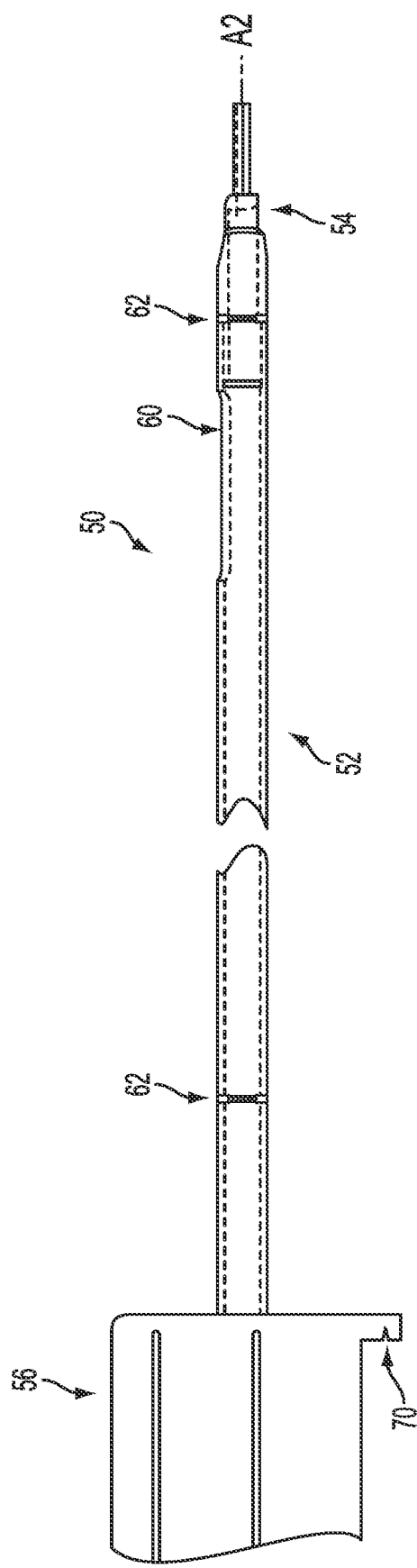
FIG. 16 is a side, partial view of one embodiment of a suture anchor driver including a shaft, an inserter, and a handle.
Figure 17:
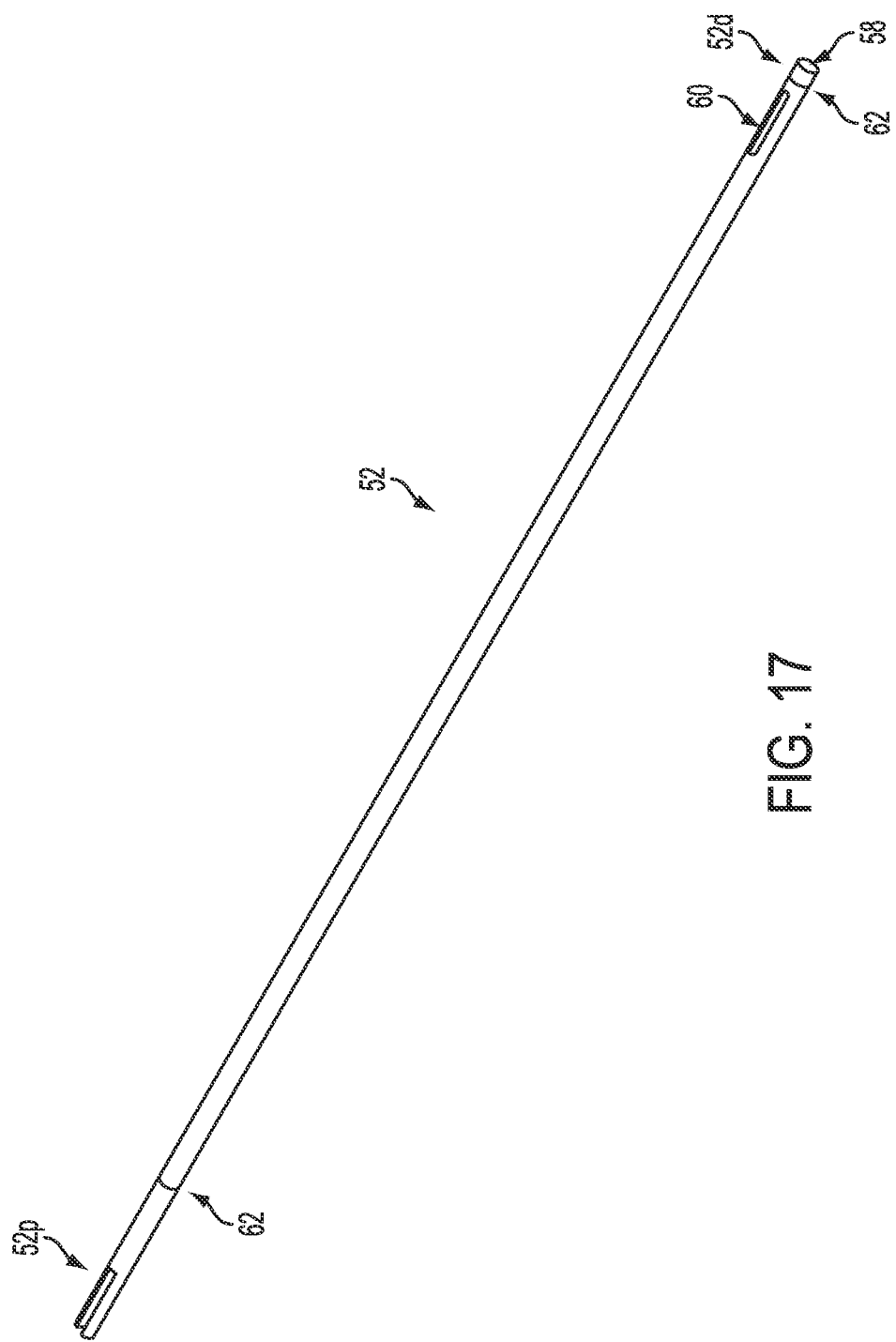
FIG. 17 is a perspective view of the shaft of the driver of FIG. 13.
Figure 18:
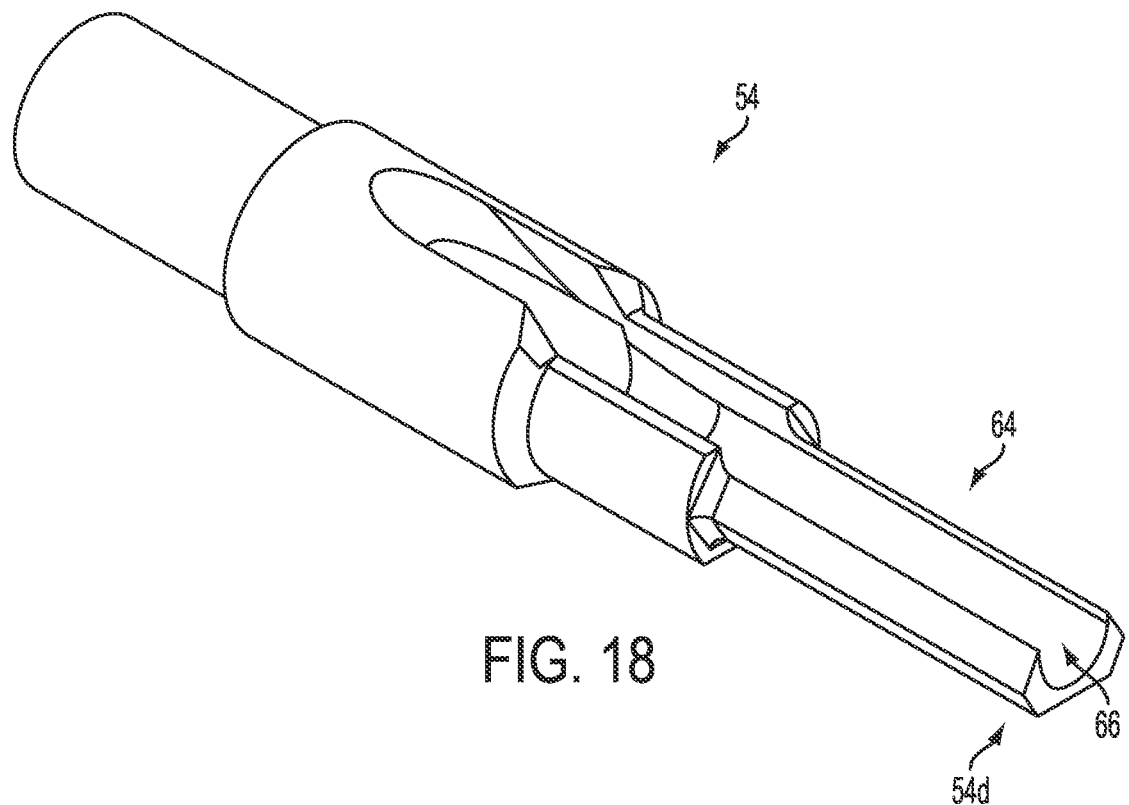
FIG. 18 is a perspective view of the inserter of the driver of FIG. 13.

The inserter 54, shown in FIGS. 16 and 18, can be configured to engage a suture anchor with a distal end 54d thereof. The inserter 54 can include a reduced diameter distal portion or tip 64 that is configured to fit within an inner lumen of a suture anchor, such as the lumen 12 of the anchor 10 of FIG. 1 or the lumen 112 of the anchor 100 of FIG. 11. The length of the tip 64 can vary, but in an exemplary embodiment the tip 64 has a length that allows it to extend through a substantial portion of the lumen in the anchor so as to maximize surface contact between the tip 64 and the anchor. For example, the length of the tip 64 can correspond to a length of the hexagonal portion of the lumen of the anchor. The shape of the tip 64 can also vary, but in an exemplary embodiment it has an asymmetrical shape that allows the tip 64 to engage the inner lumen of the anchor. By having an asymmetrical shape that corresponds to an asymmetrical shape of the anchor's inner lumen, the tip 64 can be configured to be inserted into the lumen in a single predetermined orientation relative to the anchor. In this way, as discussed further below, the rotational orientation of an anchor coupled to the inserter 54 can be known by viewing a proximal end of the driver 50, regardless of whether the anchor and/or the inserter 54 are visible, e.g., even when the anchor and the inserter 54 are partially or fully disposed within a bone tunnel. In the illustrated embodiment, the tip 32 has a generally hexagonal cross-sectional shape that complements the asymmetrical hexagonal cross-sectional shape of the lumen 12 of the anchor 10 and of the lumen 112 of the anchor 100.

The tip 64 can include one or more suture-receiving recesses or grooves 66 formed therein and extending longitudinally along the length of the tip 64. The groove(s) can be configured to seat one or more sutures, e.g., one or more of the sutures extending proximally from a suture anchor coupled to the inserter 54. As in the illustrated embodiment, the tip 64 can include only one suture-receiving groove 66 formed therein that extends along a longitudinal length thereof. The one or more grooves 66 can be in communication with the inner lumen 58 of the shaft 52, so as to help further prevent the suture(s) from interfering with insertion of the suture anchor. The one or more grooves 66 can also extend a distance beyond a proximal end of the tip 64, as shown in the illustrated embodiment. In another embodiment (not shown), a tip of an inserter can be cannulated to allow one or more suture(s) extending through the suture anchor to extend therethrough, rather than extending along an external surface of the tip as with the groove 66 in the tip 64 of FIG. 18. If the inserter tip is cannulated, the tip can have a planar sidewall configured to align with a planar sidewall of a suture anchor coupled to the inserter tip, thereby allowing the rotational orientation of the anchor coupled to the inserter tip to be known by viewing a proximal end of the driver, similar to that mentioned above.

Figure 19:
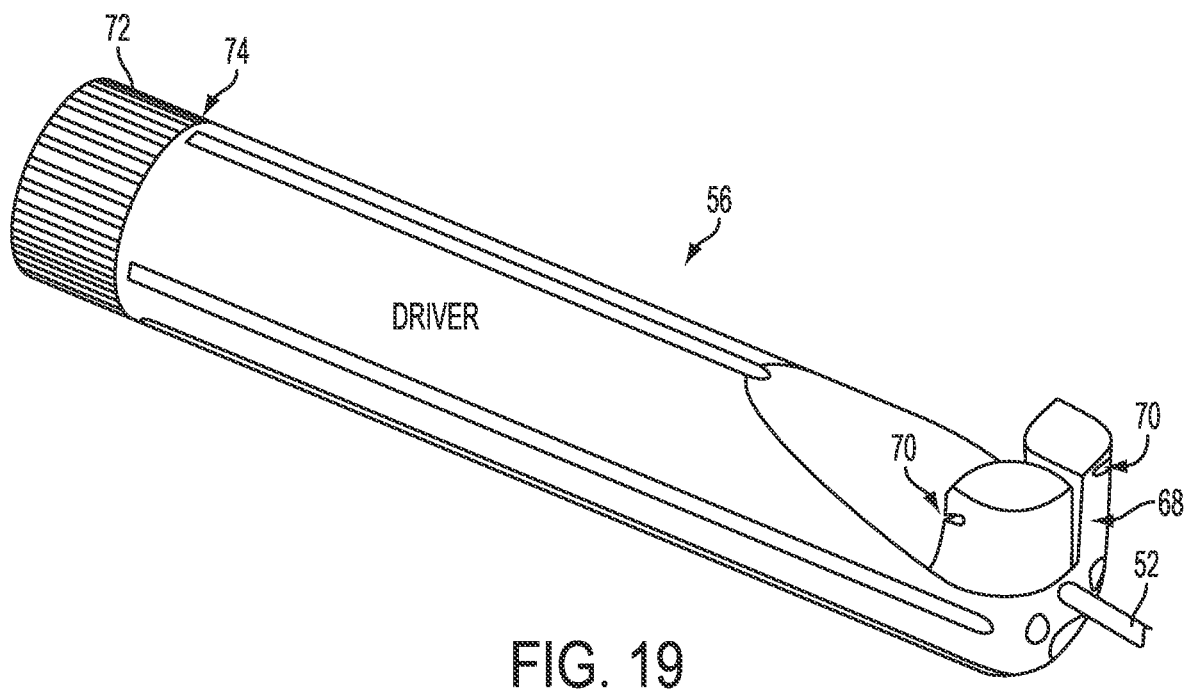
FIG. 19 is a perspective view of the handle of the driver of FIG. 13.

The handle 56, shown in FIGS. 16 and 19, can be configured to facilitate grasping and manipulation of the driver 50. The shape of the handle 56 can vary, but as in the illustrated embodiment, it can be generally cylindrical.

The handle 56 can include a suture alignment guide formed thereon that can be configured to receive and engage at least one suture, e.g., at least one stay suture extending through the shaft 52 and coupled to a suture anchor mated to the inserter 54. The suture alignment guide can also be configured to indicate the rotational orientation of an anchor coupled to the inserter 54 such that the rotational orientation of the anchor can be known by viewing the suture alignment guide, regardless of whether the anchor and/or the inserter 54 are visible. The suture alignment guide can so indicate the rotational orientation of the anchor by being in a predetermined position relative to a planar sidewall of a suture anchor coupled to the inserter 54, such as by being axially aligned therewith. The suture alignment guide and/or one or more suture channels formed in the driver can be configured to maintain tension on a suture coupled to a suture anchor coupled to the inserter 54, e.g., a tension suture, when the driver and the anchor are rotated, as discussed further below.

Figure 20:
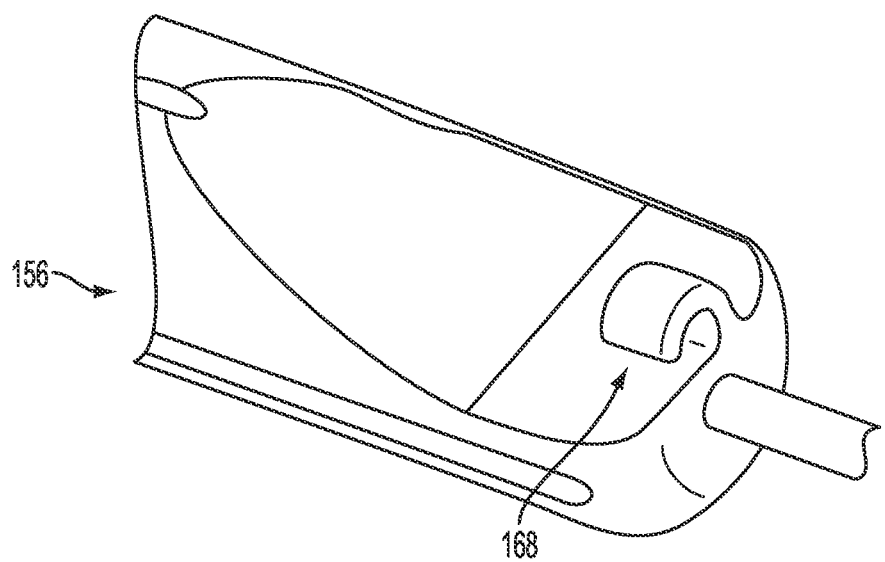
FIG. 20 is a perspective, partial view of another embodiment of a suture anchor driver.

The suture alignment guide can have a variety of configurations, sizes, and shapes. As in the illustrated embodiment, the suture alignment guide 68 can include a slot formed in a distal end 56d of the handle 56. As in the illustrated embodiment, the slot can be an elongate slot. The suture alignment guide 68 can be axially aligned with a planar sidewall of a suture anchor coupled to the inserter 54, which can allow for the rotational orientation of the anchor to be known, as discussed above, and can also allow the one or more sutures extending longitudinally along the planar sidewall to extend longitudinally along the shaft 52, either within or external to the shaft 52, to be received in the slot 68. The window 60 formed through the shaft 52 can be on an opposite side of the driver 50 as the suture alignment guide 68, which can allow one trailing end of a suture to extend along the sidewall 18 and engage the suture alignment guide 68 and the other trailing end of the suture to extend through the inner lumen 12 of the anchor 10, pass through the window 60, and couple to soft tissue. FIG. 20 illustrates another exemplary embodiment of a driver handle 156 including a suture alignment guide 168 formed in a distal end of the handle 156. The suture alignment guide 168 in this illustrated embodiment is in the form of a c-shaped or u-shaped loop.

Referring again to the embodiment of FIGS. 16 and 19, the handle 56 can also include one or more suture channels 70 configured to hold the one or more sutures received and engaged by the suture alignment guide 68 in a substantially fixed position, e.g., by crimping. The suture alignment guide 68 and the channels 70 can therefore cooperate to hold one or more sutures, e.g., one or more tension sutures, which can free hands and/or tools from having to hold the one or more sutures during a procedure until the one or more sutures are ready to be manipulated, e.g., ready to be tensioned. Thus, holding the one or more sutures can, as mentioned above, help maintain a desirable position of the one or more sutures when the driver and the anchor are rotated.

The handle 56 can also include a lock mechanism configured to lock one or more sutures, e.g., one or more stay sutures, in a fixed position relative to the driver 50 and to a suture anchor coupled to the inserter 54. The lock mechanism can have a variety of configurations, sizes, and shapes. Non-limiting examples of a lock mechanism include a clamp, a post, an adhesive, and other features for receiving and holding a suture. As in the illustrated embodiment, the lock mechanism can include a rotatable cap 72 at a proximal end of the handle 56. The cap 72 can be configured to rotate, e.g., threadably rotate, relative to a remainder of the driver 50 about a longitudinal axis A2 of the driver 50. As the cap 72 is rotated, a gap can form at a junction 74 between a distal end of the cap 72 and a proximal end of a remainder of the handle 56. One or more sutures coupled to a suture anchor coupled to the inserter 54 and extending along the shaft 52, either within or external to the shaft 52, can be positioned within the gap, and then the cap 72 can be rotated to close the gap, thereby locking the one or more sutures in place.

Figure 21:
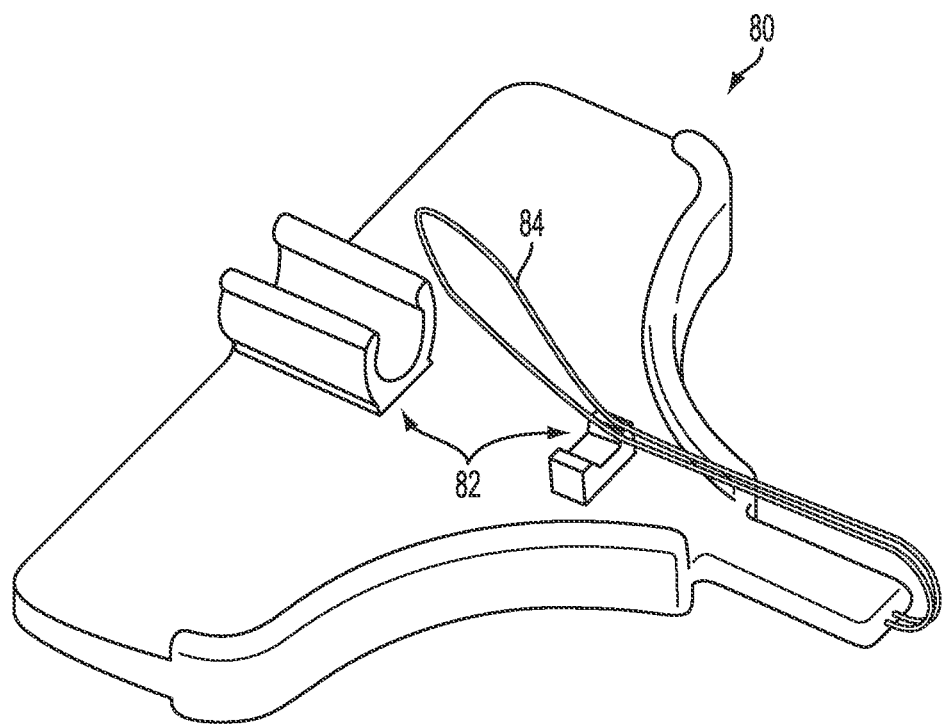
FIG. 21 is a perspective view of one embodiment of a suture threader.
Figure 22:
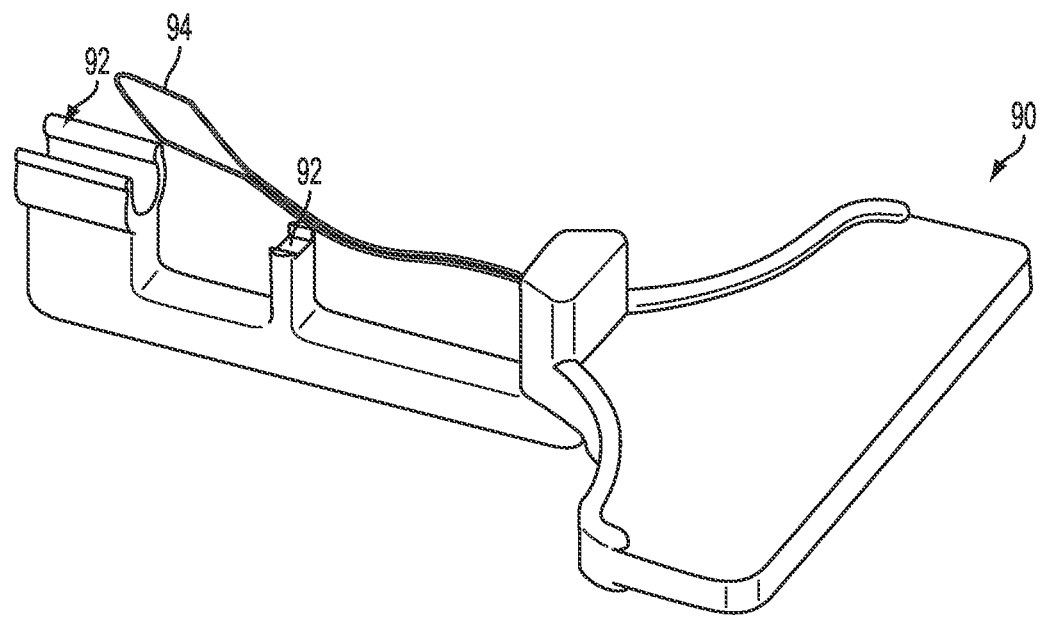
FIG. 22 is a perspective view of another embodiment of a suture threader.

A threader can cooperate with a driver and a suture anchor coupled to the driver to thread one or more sutures, e.g., one or more tension sutures, through the anchor. Generally, the threader can be configured to couple to the driver and to the anchor to feed a suture through the anchor. The threader can have a variety of configurations, sizes, and shapes. FIG. 21 illustrates an exemplary embodiment of a threader 80 configured to engage a driver and a suture anchor. The threader 80 can be configured to engage an elongate shaft of the driver via a shaft channel or groove 82 formed therein. At least one feeder wire 84 coupled to the threader 80 can be threaded through an inner lumen of the anchor. With the threader 80 coupled to the elongate shaft of the driver, the feeder wire can extend through a proximal end of the anchor and out a distal end of the anchor. At least one suture can be threaded through the feeder wire 84 located distally beyond the anchor. The threader 80 can then be pulled proximally, with the driver shaft sliding through the groove 82, to pull the suture proximally through the inner lumen of the anchor and out the proximal end of the anchor, thereby threading the suture through the anchor. The suture can then be disengaged from the threader 80, and the threader 80 can be uncoupled from the shaft and the anchor. FIG. 22 illustrates another exemplary embodiment of a threader 90 including a shaft channel or groove 92 and a feeder wire 94.

As mentioned above, the suture anchors and drivers discussed herein can be used to anchor soft tissue to bone. As also mentioned above, while the following method is described in connection with attaching soft tissue to bone, the methods and devices disclosed herein can be used in a variety of medical procedures for anchoring one structure to another.

To attach soft tissue to bone, a bore, bone hole, or bone tunnel can be formed in bone of a patient, such as by using a drill, an awl, a punch instrument, etc., as will be appreciated by a person skilled in the art. A diameter of the bone tunnel can be slightly less than a largest outer diameter of a suture anchor to be disposed within the bone tunnel, and a length of the bone tunnel can be the same as or slightly greater than a length of the suture anchor. The bone tunnel can extend fully through the cortical bone to allow the suture anchor to be fully engaged through the thickness of the cortical bone. The bone tunnel can also extend into the cancellous bone depending on the length of the suture anchor.

One or more sutures can be coupled to the suture anchor using various techniques, as previously discussed herein, and a distal tip of a driver can be coupled to the suture anchor. In an exemplary embodiment, the suture anchor is pre-loaded onto the distal tip of the driver with at least one stay suture coupled to the suture anchor and the driver. The trailing ends of the suture(s) can extend externally along the driver or they can extend through an inner lumen of the driver, as discussed above. A soft tissue can be coupled to one or more of the sutures coupled to the anchor. The driver can then be used to insert the suture anchor into the bone tunnel. The driver can be coupled to the anchor by inserting the driver into an inner lumen of the anchor or by otherwise engaging the anchor, such as by gripping an outer surface of the anchor. For non-limiting example, where the suture anchor includes one or more ridges formed thereon, the driver can be tapped or otherwise pushed distally to tap or push the suture anchor distally into the bone tunnel. The ridges will engage a wall of the bone tunnel, thereby retaining the suture anchor within the bone tunnel, e.g., through interference or compression fit. Pushing the anchor into the bone tunnel can allow one or more sutures extending along a planar sidewall of the anchor and extending along the driver to engage a suture alignment guide thereof, to remain along the planar sidewall without being compressed against the bone wall by the anchor.

Once the anchor is inserted into the bone tunnel, tension can be applied to the tension suture to pull the tissue attached thereto against the bone. If the suture anchor includes a rotatable suture-seating member, the suture-seating member will rotate as the tension suture is pulled therearound. The driver can then be rotated about its longitudinal axis to rotate the anchor within the bone tunnel from a delivery orientation to a locked orientation to lock the suture coupled to the soft tissue in a fixed position relative thereto, thereby also locking the soft tissue in a fixed position relative to the bone. Tension can be maintained on the tension suture as the driver and the anchor are rotated by holding the tension suture by hand and/or by tool, such as by engaging the tension suture with the driver's suture alignment guide. The driver and stay suture can then be removed. With the soft tissue anchored to the bone, the trailing ends of the tension suture can be secured together and the excess trimmed as is typical in these situations to complete the surgery.

Figure 23:
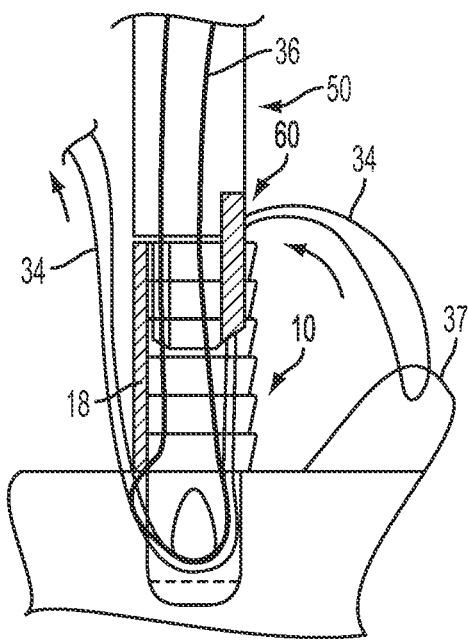
FIG. 23 is a side, partially transparent view of the driver of FIG. 16 coupled to the suture anchor of FIG. 1, the suture anchor being partially driven into bone.
Figure 24:
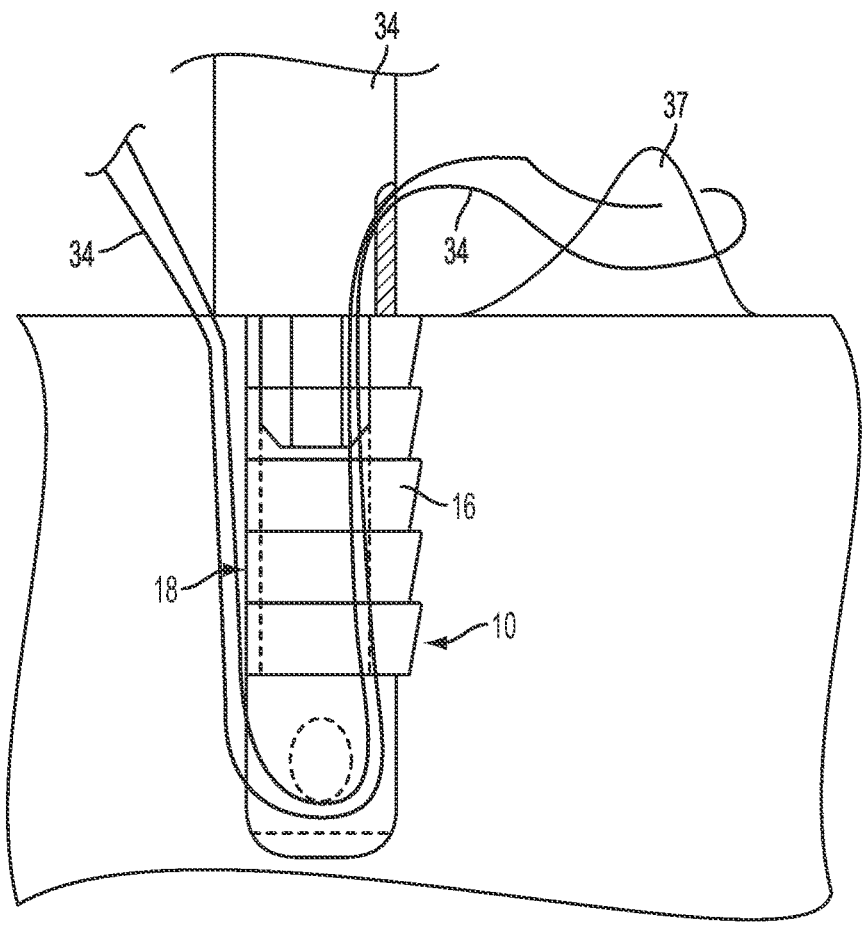
FIG. 24 is a side, partially transparent view of the driver and suture anchor of FIG. 23, the suture anchor being fully driven into the bone.
Figure 25:
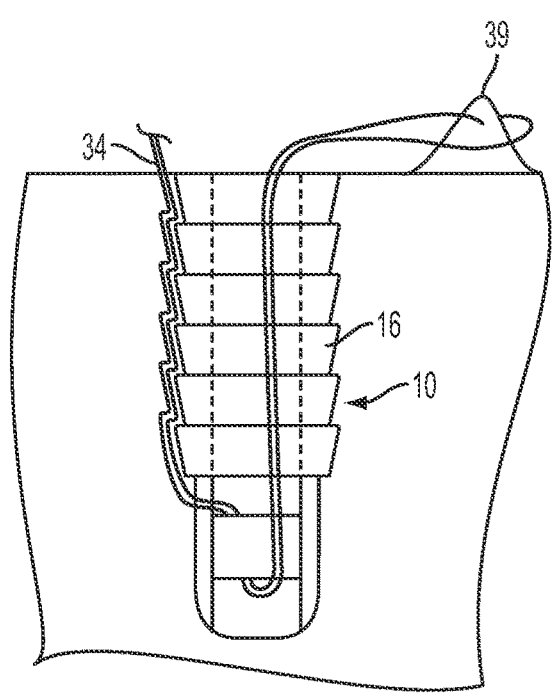
FIG. 25 is a side, partially transparent view of the suture anchor of FIG. 24, the suture anchor being fully driven into the bone and the driver being removed from the suture anchor.

An exemplary embodiment of a method for securing soft tissue to bone is illustrated in FIGS. 23-25. Although the following method is discussed with reference to the suture anchor 10 of FIG. 1 and the driver 50 of FIG. 16, any of the suture anchors and any of the drivers discussed herein can be similarly used to anchor soft tissue to bone. As shown in FIG. 23, the anchor 10 in a delivery orientation can have the stay suture 36 and the tension suture 34 extending through the inner lumen 12 of the anchor 10. The stay suture 36 can extend through the lumen of the driver 50 to the cap 72, which locks the stay suture 36 in position relative to the driver 50 and the anchor 10. A first portion of the tension suture 34 can extend along the planar sidewall 18 and engage the suture alignment mechanism 68 (not shown in FIG. 23) of the driver 50. The first portion of the tension suture 34 can also engage at least one of the channels 70 (not shown in FIG. 23) of the driver 50. A second portion of the tension suture 34 can extend through the inner lumen 12 of the anchor 10 and briefly into the lumen 58 of the shaft 52 before exiting the driver 50 through the sidewall window 60. The tension suture 34, e.g., an end extending through the window 60, can be coupled to a soft tissue 37, e.g., labrum, such as by being passed therethrough with a needle, as will be appreciated by a person skilled in the art. The tension suture 34 can be attached to the soft tissue 37 before or after the tension suture 34 is threaded through the anchor 10, e.g., using a threader, but in an exemplary embodiment, the soft tissue 37 is attached to the suture 34 before it is threaded through the anchor 10.

As shown in FIG. 24, the anchor 10 in the delivery orientation having the soft tissue 37 coupled thereto via the tension suture 34 can be inserted into a bone tunnel. The bone tunnel can be formed in the bone before or after the tension suture 34 is coupled to the anchor 10. In an exemplary embodiment, the driver 50 can be tapped or pushed distally and the anchor 10 can be zip-lined along the tension suture 34 to advance the anchor 10 distally into the bone tunnel. As mentioned above, the anchor 10 can be inserted any depth into the bone tunnel, such as substantially flush or sub-flush with the proximal-most end of the bone tunnel. The distal depth marking 62 (not shown in FIG. 21) on the driver shaft 52 near the driver inserter 54 can help visually indicate when the anchor 10 has been inserted substantially flush or sub-flush with the proximal-most end of the bone tunnel. In an exemplary embodiment, the driver 50 can be tapped until the distal depth marking 62 is substantially flush with the proximal-most end of the bone tunnel, thereby indicating that the suture anchor 10 has been inserted substantially sub-flush into the bone tunnel.

With the anchor 10 inserted into the bone tunnel, the soft tissue 37 can be tensioned by pulling the tension suture 34 in a proximal direction, e.g., by pulling the end of the suture 34 not attached to the soft tissue 37. The planar sidewall 18 of the anchor 10 allows the tension suture 34 to slide within the bone tunnel to tension the soft tissue relative to the bone, e.g., to slide within a gap or suture-receiving space between a bone wall defining the bone tunnel and the planar sidewall 18 of the anchor 10. The soft tissue 37 therefore need not be tensioned prior to inserting the anchor 10 into the bone tunnel. Instead, the planar sidewall 18 of the anchor 10 can allow the soft tissue 37 to be tensioned after the anchor 10 has been inserted substantially flush or sub-flush with a proximal-most end of the bone tunnel. By allowing the soft tissue 37 to be tensioned after insertion of the anchor 10 into the bone tunnel, the soft tissue 37 can be more snugly pulled against the bone, thereby facilitating healing.

With the soft tissue 37 desirably tensioned, the anchor 10 can be rotated about its longitudinal axis A to move from the delivery orientation to a locked orientation to capture, compress, or crimp the tension suture 34 between the at least one bone-engaging surface feature 16 and the bone wall, as shown in FIG. 25. In other words, the anchor 10 can be rotated such that the at least one bone-engaging surface feature 16 enters the gap in which the tension suture 34 is located to press the tension suture 34 against the bone wall, locking it between the anchor 10 and the bone. As mentioned above, a friction force between the tension suture 34 and the one or more bone-engaging surface features 16 can be greater than a friction force between the tension suture 34 and the sidewall 18. In other words, the tension suture 34 can be subject less friction or resistance when the anchor 10 is in the delivery orientation within bone than when the anchor 10 is in the locked orientation within bone. The tension suture 34 can therefore be tensioned relatively easily when it is positioned between the sidewall 18 and the bone wall as opposed to when it is positioned between the one or more bone-engaging surface features 16 and the bone wall.

The anchor 10 can be rotated within the bone tunnel by rotating the driver 50 attached thereto about the longitudinal axis A2 of the driver 50. Because the suture alignment guide 68 of the driver 50 can be axially aligned with the planar sidewall 18 of the anchor 10 when the anchor 10 is coupled to the distal tip 64 of the driver 50, an amount of driver rotation can be easily visually monitored, thereby preventing over-rotation and under-rotation of the driver 50 and ensuring that the at least one bone-engaging surface feature 16 non-movably locks the tension suture 34 between the anchor 10 and the bone wall. The driver 50, and hence the anchor 10, can be rotated any amount clockwise or counter-clockwise to so lock the tension suture 34. In an exemplary embodiment, the driver 50 and the suture 10 can be rotated at least a quarter turn either clockwise or counterclockwise but less than a full turn, e.g., in a range of about 90 to 270 degrees, e.g., about 90 degrees or about 180 degrees. As mentioned above, when the driver 50 and the anchor 10 are rotated, a first friction force between the tension suture 34 and the relatively rough bone wall can be less than a second friction force between the tension suture 34 and the planar sidewall 18, thereby allowing and urging the tension suture 34 to not rotate with the sidewall 18 but instead become trapped between the bone wall and the at least one bone-engaging surface feature 16. As also mentioned above, the sidewall in some suture anchor embodiments can have one or more surface features, which can provide some resistance to a suture when the anchor is rotated within a bone hole such that the suture is not slidable along the sidewall, but the anchor can nevertheless be configured such that a first friction force between the suture and a surface of the bone hole can be less than a second friction force between the suture and the sidewall. When the driver 50 and the anchor 10 are rotated, the tension suture 34 can be held by hand and/or engaged with the suture alignment guide 68 and/or at least one of the channels 70 formed in the driver handle 50, which can help maintain the tension of the tension suture 34 during rotation. The tension of the tension suture 34 can additionally or alternatively be maintained during rotation because the first friction force between the tension suture 34 and the relatively rough bone wall can be greater than the second friction force between the tension suture 34 and the planar sidewall 18.

Following rotation of the anchor 10 and locking of the tension suture 34 between the bone surface of the bone tunnel and the one or more bone-engaging surface features 16, the driver 50 and the stay suture 36 can be removed. The stay suture 36 can be removed from the anchor 10 by unlocking the stay suture 36 from the driver 50, e.g., by rotating the cap 72. The stay suture 36 can then be pulled proximally to be removed from the anchor 10. The driver 50 can be removed from the anchor 10 by pulling the driver 50 proximally to withdraw the inserter 54 from within the inner lumen 12 of the anchor 10. The trailing ends of the tension suture 34 extending proximally from the bone tunnel can be secured together and the excess trimmed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   inserting a suture anchor into a bone hole, a suture extending through an inner lumen of the suture anchor and extending along an exterior of the suture anchor, the suture anchor including a substantially D-shaped cross sectional shape in at least a proximal portion thereof, the suture anchor being in a first orientation in the bone hole in which a bone-engaging surface feature formed on the suture anchor engages bone;
   with the suture anchor in the first orientation in the bone hole, tensioning the suture and thereby causing the suture to slide along the exterior of the suture anchor relative to the bone; and
   moving the suture anchor from the first orientation in the bone hole to a second orientation in the bone hole in which the suture is engaged between the bone and the bone-engaging surface feature such that the suture is prevented from sliding along the suture anchor relative to the bone.

2. The method of claim 1, wherein the substantially D-shaped cross sectional shape comprises an external curved surface of the suture anchor and an external planar surface of the suture anchor, the suture anchor in the first orientation in the bone hole having the suture extending along the external planar surface, and the suture anchor in the second orientation in the bone hole having the suture extending along the external curved surface.

3. The method of claim 1, wherein moving the suture anchor comprises rotating the suture anchor about a longitudinal axis thereof.

4. The method of claim 1, wherein when the suture anchor is in the first orientation in the bone hole the suture extends through an opening formed through a sidewall of the suture anchor, and the tensioning of the suture also causes the suture to slide within the opening.

* * * * *